United States Patent
Heffner

(10) Patent No.: US 9,248,012 B2
(45) Date of Patent: Feb. 2, 2016

(54) MESH BASED FLUID DELIVERY PROSTHESIS AND METHOD OF USE

(76) Inventor: Jeremy J. Heffner, Ypsilanti, MI (US)

( * ) Notice: Subject to any disclaimer, the term of this patent is extended or adjusted under 35 U.S.C. 154(b) by 705 days.

(21) Appl. No.: 13/464,336

(22) Filed: May 4, 2012

(65) Prior Publication Data

US 2012/0283692 A1    Nov. 8, 2012

Related U.S. Application Data

(60) Provisional application No. 61/483,213, filed on May 6, 2011.

(51) Int. Cl.
| | |
|---|---|
| *A61F 2/02* | (2006.01) |
| *A61F 13/00* | (2006.01) |
| *A61F 2/00* | (2006.01) |
| *A61M 37/00* | (2006.01) |

(52) U.S. Cl.
CPC .............. *A61F 2/0063* (2013.01); *A61M 37/00* (2013.01); *A61F 2250/0068* (2013.01)

(58) Field of Classification Search
CPC . A61M 5/14276; A61M 31/00; A61M 37/00; A61F 2/0063; A61F 2250/0068; A61F 2210/0004
See application file for complete search history.

(56) References Cited

U.S. PATENT DOCUMENTS

| | | | |
|---|---|---|---|
| 5,176,692 A * | 1/1993 | Wilk et al. | 606/151 |
| 2004/0234576 A1* | 11/2004 | Martin et al. | 424/426 |

OTHER PUBLICATIONS

Definition of mesh Oxford English Dictionary accessed Apr. 6, 2015.*
Parker et al. (Current Surgery; vol. 63/No. 4; Jul./Aug. 2006).*

* cited by examiner

*Primary Examiner* — Abigail Fisher
*Assistant Examiner* — Jessica Kassa
(74) *Attorney, Agent, or Firm* — Robert G. Lev

(57) ABSTRACT

A fluid delivery system is used for the treatment of subcutaneous hernia sites and includes a bioabsorbable polymer fabric mesh layer and a bioabsorbable and permeable bladder attached to the upper side of the fabric mesh layer. Fluid from the bladder is diffused through pores communicating between the bladder and the fabric mesh layer so as to be dispersed to underlying tissue.

11 Claims, 3 Drawing Sheets

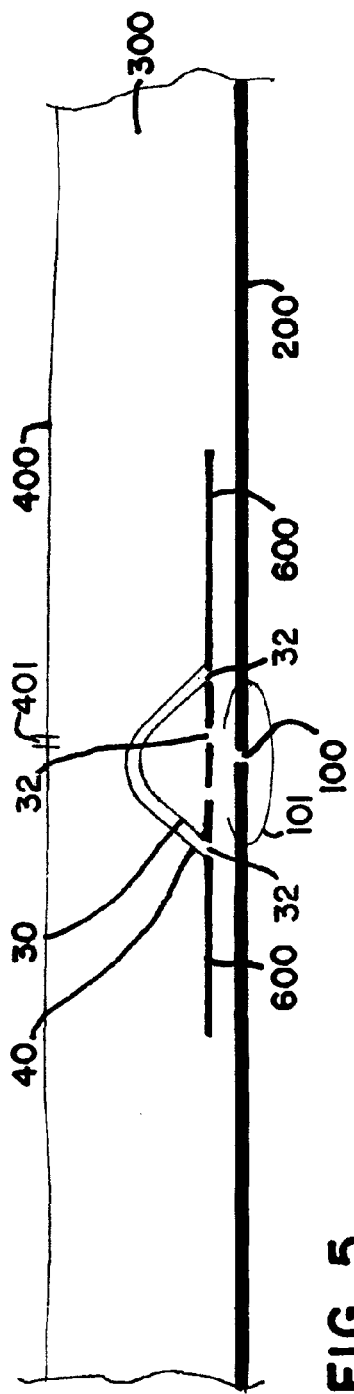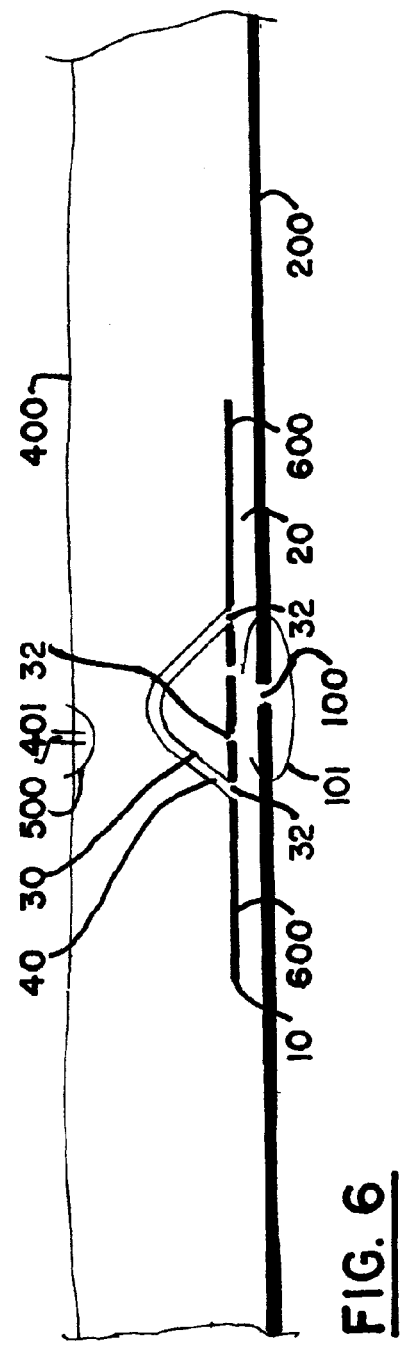

MESH BASED FLUID DELIVERY PROSTHESIS AND METHOD OF USE

PRIORITY INFORMATION

The present invention claims priority to U.S. Provisional Application No. 61/483,213 filed on May 6, 2011, making reference to and incorporating herein, the same in its entirety.

FIELD OF THE INVENTION

The present invention relates generally to the field of self-contained fluid delivery systems, implantable into a patient, for the prevention and treatment of hernias, and the like, and which is operable to deliver medicaments to the selected implantation site. In particular, the present invention is directed to apparatus and technique for generally treating and strengthening suspect areas of the fascia such as that found around wounds and the like.

BACKGROUND OF THE INVENTION

In the United States and across the world, a major complication associated with surgical procedures is the development of an incisional hernia. As high as 10% of open abdominal operations will be complicated by the development of incisional hernias. An incisional hernia occurs when a weakness in the muscle of the abdomen allows the tissues of the abdomen to protrude through the muscle. The hernia appears as a bulge under the skin, and can be painful or tender to the touch. In the case of an incisional hernia, the weakness in the muscle is caused by the incision made in a prior abdominal surgery. An incisional hernia may be small enough that only the peritoneum, of the lining of the abdominal cavity, pushes through. In severe cases, portions of organs may move through the muscle.

Repair rates of incisional hernias are even worse with some recurrence rates approaching 50%. Many biologic technologies are being developed to decrease the rate of hernia formation as well as to repair the hernias if they do occur.

Studies are currently being performed with indwelling catheter-based technologies allowing for drug delivery to the incisional site wherein the catheter provides saturation of the wound bed with various medicament-containing liquids. The distal end of the catheter is inserted in or around the wound site, secured to the patient with surgical sutures, surgical adhesive, bandages or the like, leaving an accessible proximal end portion of the catheter to allow for the infusion of therapeutic liquids through one or more proximal catheter ports.

Unfortunately, it commonly occurs that indwelling catheters lead to infections caused by cutaneous organisms mesh seeding along the catheter line into the incisional area at the site of implantation. Catheter infection, defined as the entrance of microorganisms at the site around or in the catheter, is a serious complication, particularly when a mesh is implanted for hernia repair. Microorganisms invariably gain access to the tract of the sheath and the catheter at the skin surface and grow inwards toward the surgical hernia area, contaminating the surgical site. The longer the duration of a transcutaneous catheter, the greater the risk of infection.

An infection arising from an indwelling transcutaneous catheter is an especially severe complication in surgical procedures involving hernia repair where a mesh is implanted to secure a hernial rupture. Invariably, the infection arising from the indwelling catheter will contaminate the entire area including the implanted mesh, giving rise to life threatening infections. Often, the entire infected mesh has to be removed as well as the infected tissue surrounding it.

Currently, there are no universal self-contained implantable hernia repair devices that allow for the testing and delivery of medicaments directly to the hernia repair site.

Accordingly, there is a need for a comprehensive hernia control, prevention, treatment and a system that avoids or, at least, decreases the chances of infection while strengthening the tissue surrounding hernias, or potential hernias. Such a system would provide general, as well as specific, remedies for the drawbacks of the conventional art.

SUMMARY OF THE INVENTION

It is a major object of the present invention to comprehensively treat hernias or potential hernia sites, using both structural reinforcement and biological reinforcement.

It is a further object of the present invention to provide a wound treatment system that substantially reduces the incidence of infection.

It is an another object of the present invention to provide a hernia treatment system that can be configured to a wide variety of different shapes and sizes of wounds or potential hernia sites.

It is an additional object of the present invention to provide a fluid delivery system for hernia sites, having the capability of automatically delivering fluids with therapeutic medicants to a wide area around a hernia site, without increased invasiveness.

It is still a further object of the present invention to provide a fluid delivery system equally capable of treating both incisional hernias and potential hernia sites.

It is again an additional object of the present invention to provide a fluid delivery system which is adapted to encourage ingrowth of collagen at or near the site of a hernia, or a potential hernia.

It is yet a further object of the present invention to provide a fluid delivery system which can also provide additional structural stability to the site of a hernia or a potential hernia.

It is still another object of the present invention to provide a self-contained, fully implantable device that can deliver medicaments to a wound site without the use of transcutaneous catheters.

It is again a further object of the present invention to provide a structurally reinforcing hernia incisional treatment system which is fully absorbable.

It is still another object of the present invention to provide a treatment system for hernias, which can be arranged in a wide variety of different postures, orientations, sizes, and configurations.

It is still an additional object of the present invention to provide a minimally invasive treatment system for reinforcing potential hernia sites.

It is yet a further object of the present invention to provide a hernia treatment system that can provide medicants from beneath the hernia site.

It is again a further object of the present invention to provide a system for hernia repair using standard surgical techniques.

These and other goals and objects of the present invention are achieved by a fluid delivery system for the treatment of subcutaneous hernia sites. The system includes a bioabsorbable polymer fabric mesh layer which is substantially planar in configuration, and is arranged with an upper side and a lower side. This system also includes a bioabsorbable, impermeable bladder attached to the upper side of the mesh layer and in fluid communication therewith.

Another embodiment of the present invention is encompassed by a method of treating fascia at an incision site. The method includes the first step of opening the skin and subcutaneous fat at the incision site. Then a device including a bioabsorbable polymer fabric mesh layer and a connected bioabsorbable bladder is placed under the subcutaneous fat. Finally, liquid is dispersed from the bladder through the polymer fabric mesh layer and to the fascia at the incision site.

BRIEF DESCRIPTION OF THE DRAWINGS

FIG. 5 is a side view of a second embodiment of the present invention, depicting the environment in which the invention is used.

FIG. 6 is a side view of a third embodiment, depicting an inverted fluid delivery arrangement located underneath the fascia.

DESCRIPTION OF THE PREFERRED EMBODIMENTS

Figure 1:
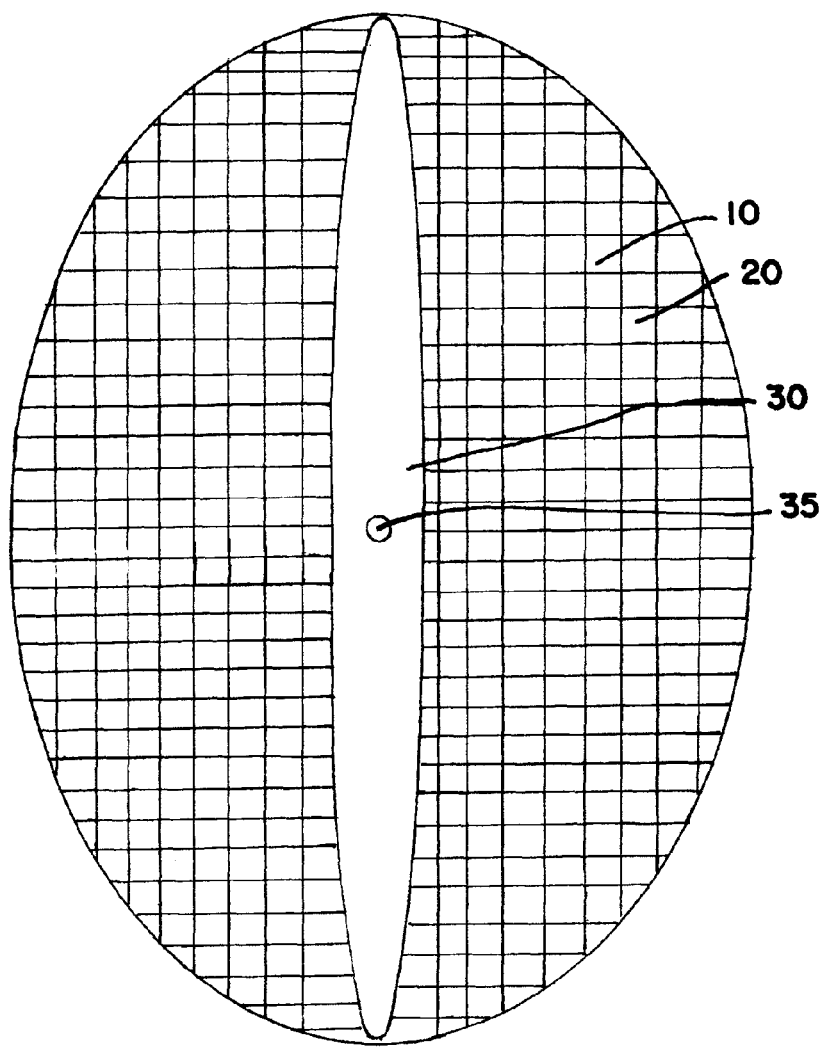
FIG. 1 is a top view of a first embodiment of the inventive hernia treatment system.

To meet these and other objectives, numerous studies and research have been conducted to develop the present invention. This is an implantable, self-contained, mesh based system for the delivery of medicaments (such as antibiotics, growth factors, cell based technologies, etc.), directly to a hernia or potential hernia site. The system includes a bioabsorbable polymer fabric mesh layer 10 having a bioabsorbable porous underlayment 20 for tissue ingrowth. The inventive hernia repair system also includes a fluid impermeable central bladder 30, also fabricated from bioabsorbable material, situated centrally on top of the mesh layer 10. The portion of the mesh layer 10 covered by the bladder 30 contains small capillary pores 32 to allow for fluid diffusion from the bladder, through the mesh and underlayment 20, and into the surgical site 100.

The inventive hernia treatment system allows for fluid diffusion throughout the hernia repair site 100, due to its use of capillary dispersion from bladder 30. The overall structure (including mesh layer 10 and bladder 30) of the hernia repair system may be configured to any size or shape needed by the surgeon immediately prior to surgical implantation.

The use of bladder 30 permits the entire system to be installed subcutaneously to provide medicating fluid over a wide area with minimal invasiveness. This constitutes a major improvement over the conventional use of catheters. Also, through the use of the bioabsorbable mesh material fabric, the mesh layer 10 and the bladder 30 also provide a level of structural stability not found in other systems for providing subcutaneous medication to the fascia.

For purposes of the present invention, a hernia site 100 is construed to be an actual tear in the fascia, (usually a circular opening), or a weak area at which a hernia might develop. The present invention is most appropriate for incisional hernias such as that depicted in FIG. 5, which includes the entire environment in which the inventive fluid delivery system for hernia treatment is used.

Figure 2:
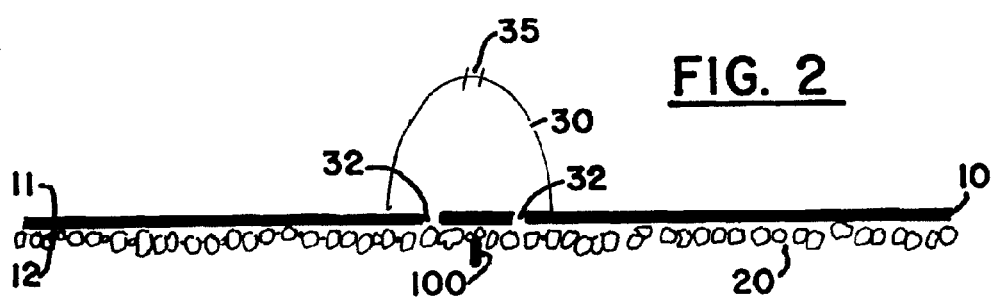
FIG. 2 is a side view of the hernia treatment system of FIG. 1.

With reference to the most basic embodiment of FIGS. 1 and 2, the inventive hernia treatment system 1 comprises a bioabsorbable polymer fabric mesh layer 10 having a first side 11 and a second side 12. A bioabsorbable polymer bladder 30 is attached to the first side 11 and located approximately centrally thereon. Bioabsorbable porous underlay 20 is attached to a second side 12 of the bioabsorbable fabric mesh 10. As shown in FIG. 2, bioabsorbable fluid impermeable bladder 30 is in fluid communication with the porous underlay through one or more capillary pores 32.

Fluid impermeable bladder 30 is attached to bioabsorbable fabric mesh 10 by gluing or heat sealing the perimeter thereof. Filling of bladder 30 may be performed during surgery using a syringe of other type of filling apparatus. A syringe (not shown) may be inserted from the distal (skin) side of the device into bladder 30. Alternatively, bladder 30 may be manufactured in a filled condition containing the therapeutic medicaments.

Fluid impermeable bladder 30 is preferably made from a bioabsorbable fluid impermeable material, such as polylactic acid, polyglycolic acid, polycaprolactone, polydioxanone, trimethylene carbonate, copolymers or blends thereof. One preferred polymer is a polylactic acid polymer which can be a homopolymer of lactic acid and/or a block, graft, random, and/or copolymer of lactic acid including D-polylactic acid, L-polylactic acid, D,L-polylactic acid, meso-polylactic acid, and any combination of the fore mentioned materials, depending on the specified/required rate of biodegradability. The polylactic acid polymer preferably contains one or more biodegradable plasticizers such as citric acid esters and the like. U.S. Patent Application 2010/0257657 A1, is expressly incorporated herein by references, and discloses many variations of bioabsorbable polylactic acid polymers which have sufficient tensile strength and elasticity suitable for use in the present invention.

Therapeutic liquid medicaments useful for bladder 30 include but are not limited to antibiotics, growth factors, cell-based technologies, analgesics, anti-inflammatory agents, hemostatic agents, anti-microbials, anti-septics and the like and combinations thereof.

Another advantage of the present invention is that different types of liquid medicaments can be used at various times during the surgical and/or healing process. This is done very simply be using a syringe to insert a different fluid through port 35. In the alternative, the syringe could even be used to pierce the membrane of bladder 30 to provide the additional therapeutic fluid. This technique of refilling or recharging bladder 30 provides greater variation with less invasiveness than is possible with conventional catheters. Further, because of the bladder 30 structure, far greater dispersion of therapeutic fluid can be achieved than with a single catheter.

Bioabsorbable porous underlay 20 is preferably made of collagen porous material such as Surgisis™ or Alloderm™. Surgisis™ provides a natural matrix with a three-dimensional structure and biochemical composition that attracts host cells and support tissue remodeling. Surgisis™ is a bioprosthesis made of resorbable biomaterial. It is a treated xenograft material commercially available from Cook Biotech, Bloomington, Ind. Alloderm™ is another three-dimensional structured biograft of extracellular matrix derived from human tissue.

Other types of bioabsorbable porous materials useful for porous underlay 20 include but are not limited to block copolymers of polyglycolic acid and trimethylene carbonate (PGA/TMC), polylactic acid/polyglycolid acid (PLA/PGA), or other homopolymers, copolymers or polymer blends derived from other biocompatible bioabsorbable monomeric components. Such homopolymers or copolymers can be comprised of varying amounts of one or more of the following monomer examples: glycolide, d,l-lactide, l-lactide, d-lactide, p-dioxanone (1,4-dioxane-2-one), trimethylene carbonate (1,3-dioxane-2-one), e-caprolactone, gamma.butyrolactone, delta.-valerolactone, 1,4-dioxepan-2-one, and 1,5-dioxepan-2-one. Other bioabsorbable polymeric constituents may include polyethylene glycol, polypropylene glycol, N-vinyl pyrrolidone, amino acids, anhydrides, orthoesters, phosphazines, amides, urethanes, and phosphoesters. Alternative copolymers may possess, in whole or in part, combinations of block, segmented, random, alternating, or statistical polymeric construction characteristics.

Bioabsorbable polymer fabric mesh layer 10 is preferably a fluid impermeable or slightly permeable bioabsorbable material made from thin fibers woven into an impermeable mesh made from collagen, lactides, glycolides, or co-weaves of such materials. One such material that has been used in successful experiments is Phasix®. Bioabsorbable polymer fabric mesh may also be rendered impermeable by coating with another impermeable polymer, such as polylactic acid or slowly dissolvable bioerodible gels.

The nature of the Phasix® mesh is such that it provides a high level of tensile strength. This is crucial in healing hernias or reinforcing weak spots that might develop into hernias. Because of the tensile strength provided by the Phasix® mesh, a wide area can be covered to provide structural support for the weak area through the Phasix® mesh.

Assembly of the device is accomplished using heat sealing or bioabsorbable adhesives. Examples of bioabsorbable adhesives include but are not limited to fibrin glue, collagen, albumin, marine derived adhesives, cyanoacrylate and any of the tissue adhesives known in the art.

Bioactive compounds may be added to bioabsorbable fabric mesh layer 10 and/or porous underlay 20. These compounds may be added as is known in the art, such as in the form of sustained release microparticles, powders, beads, matrices, coatings or layers, dipping, etc.

Once the fluid delivery system is implanted, the surgical site 100 may be completely closed, such as with staple 500 in skin 400 (FIGS. 5 and 6). Accordingly, the hernia repair system creates a self-contained, fully implantable arrangement that facilitates fluid diffusion throughout the hernia repair site 100 from bladder 30 through capillary pores 32 in the bladder and corresponding pores 32 in the polymer mesh layer 10. Due to its use of capillary dispersion, the edges of the hernia repair system are may be cut to any size needed by the surgeon immediately prior to surgical implantation. The components (polymer mesh layer 10 and bladder 30) of the hernia repair device is slowly biodegradable and disappears within about 50 to 60 days.

It should be noted that while bladder 30 can be fed using a hypodermic needle, there are other techniques that can be used to add or remove liquids from bladder 30. One such technique is the use of a port 35. This can be almost any suitable medical arrangement, including but not limited to a special area for receiving hypodermic needles, a port for receiving spouts or the like.

Figure 3:
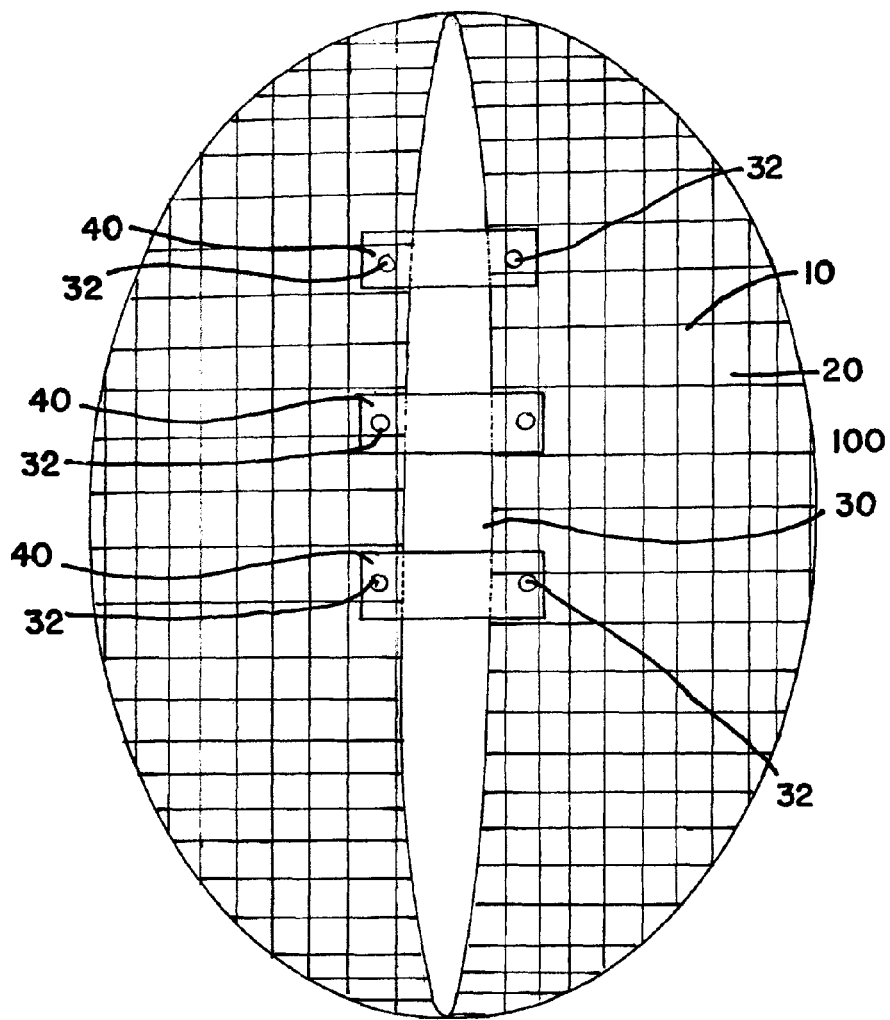
FIG. 3 is a top view of a second embodiment of the inventive hernia treatment system.
Figure 4:
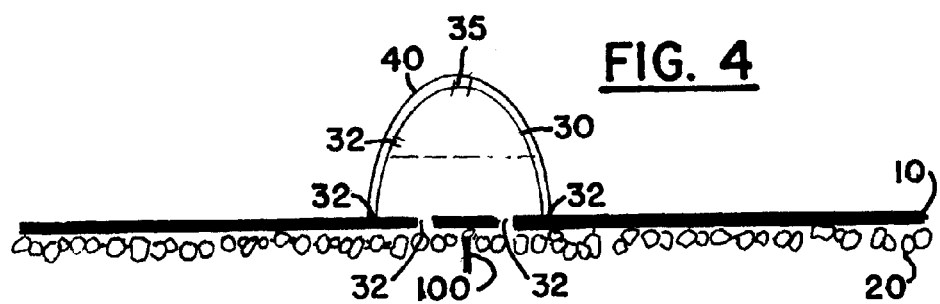
FIG. 4 is a side view of second embodiment of the FIG. 3 embodiment of the hernia treatment system.

A second embodiment is depicted in FIGS. 3 and 4. This embodiment includes the addition of hollow bands 40, which can be used to hold additional liquid to provide additional irrigation to the tissue beneath the overlying polymer mesh layer 10. Of course, each band 40 will have a corresponding pore 32 in the overlying mesh 10 beneath the band 40. There can also be additional pores 32 connecting the interior of bands 40 with the interior of bladder 30. These pores allow the liquid in the bladder 30 to migrate into the bands by capillary action.

While bands 40 are depicted as closely following the contours of bladder 30, it is not necessarily the case. Rather, the bands 40 can be extended well beyond the bladder 30 in order to spread fluid from the bladder over a wider area of the fabric mesh layer 10. There will be open ends of each of the bands 40, which will be connected to corresponding pores (approximately 1 mm in diameter) in the polymer mesh layer 10. The bands can be of any size deemed appropriate for the particular treatment site. Further, a greater or lesser number of connecting pores 32 between band 40 and the bladder 30 can also be employed, depending the desired rate of fluid dispersion over the treatment site 100.

Any number or configuration of bands 40 and corresponding pores 32 can be used in conjunction with bladder 30. The bladder 30 can be of any size appropriate for treating the tissue surrounding the wound site 100. Further, the pores 32 in polymer mesh 10 can be configured in any manner appropriate for the particular area of tissue being covered.

FIG. 5 is a side view of the present invention depicted within its normal treatment environment. In particular, the entire system is implanted subcutaneously immediately over the wound site 100 in fascia 200. The overall system (including bladder 30 and polymer mesh layer 10, as well as underlay 20), is implanted beneath or within the subcutaneous fat 300. The entry point, incision 401 in skin 400, is closed with staple 500. The entire system is connected in place by sutures 600 through the fascia 200 and the polymer fabric mesh layer (made of Phasix®) 10. The use of the implanted Phasix® mesh layer 10 over a wide area (with respect to the incision site 100) provides a great deal of structural stability to help hold the incision 100 together, aiding incision suture 101.

Pores 32 in the bottom of bladder 30 permit the liquid contained in the bladder 30 to easily diffuse through the collagen layer 20 and into the fascia 200 near incision 100. As previously described, pores 32 in the bladder 30 provide movement of the fluid in the bladder 30 into the bands 40 through complementary pores 32 in the band 40 via capillary action. This allows fluid from bladder 30 to be distributed well beyond the dimensions of the bladder 30. Accordingly, by using extended length bands 40, fluid from bladder 30 can be delivered to the very edges of the Phasix® fabric mesh 10, for example at sutures 600.

It should be noted that with a typical hernia, the size of bladder 30 is 0.3 cm wide, 1.5 cm tall and approximately 1-3 cm in length. The ends of bladder 30 are typically pointed so that the overall shape of the bladder as seen from above is a pointed oblong or oval. Also, typically, the mesh layer 10 extends approximately 3 cm beyond the bladder 30. It should be noted that relative sizes depicted in the drawings are merely representative and are not to scale or to proportion. Further, bladder 30, as well as the polymer fabric mesh layer 10, can be of any size or shape appropriate for the hernia, wound or treatment site. Further, while the bands 40 are shown to conform to the size and shape of bladder 30, this is not necessarily true. One major advantage of bands 40 is that they can extend well beyond bladder 30, and even to the edges of polymer fabric mesh layer 10.

FIG. 6 is a side view very similar to FIG. 5. The exception is that an inverted version of the present fluid distribution system is surgically implanted beneath the fascia incision 100. This is done using standard surgical techniques. The inverted fluid distribution system 900 is sewn to the fascia using sutures 600 in the same manner as the fluid distribution system in the upright orientation. In this manner, fluid from the inverted bladder 30 can be dispersed directly beneath incision 100 to facilitate healing. The collagen underlayer 20 found in the upright arrangement is optional for the inverted arrangement since it may slow the dispersement of fluids from bladder 30 to the fascia 200 near incision 100.

The entire combination of bladder 30 and mesh layer 10 can be inserted using standard techniques. This includes coating the mesh layer 10 and bladder 30 combination with an omega-3 fatty acid. Because capillary action is responsible for the movement of liquid from bladder 30 through pores 32 and into the bands 40, the liquid is easily dispersed through pores 32 in any part of the bladder 30 to the desired portion of fascia 200. The bands 40 can be selected and arranged to channel fluids from bladder 30 to any portion of the fascia 200, near the incision 100.

The use of both the inverted configuration 900 and the upright configuration maximizes the amount of fluid medicament that can be delivered to the wound site 100. This approach is feasible because all of the materials are bioabsorbable so that they do not have to be removed at a later time. The result is a minimum of invasiveness with a maximum of fluid medicaments extending over as wide an area as is desired around and under the incision 100. None of the risks of a conventional catheter are incurred with the present system.

It should be understood that the relationship in size and proportion between bladder 30 and polymer fabric mesh layer 10 can be any that are found suitable by the surgeon for a particular treatment site. Likewise, the length and number of bands 40 can also be selected to disperse fluid to virtually any desired area selected by the surgeon. As a result, virtually any arrangement employing the elements described supra can be deployed within the concept of the present invention.

While a number of embodiments have been described for purposes of examples, the present invention is not limited thereto. Rather, the present invention should be considered to include any and all various, derivations, adaptations, and embodiments that would occur to one skilled in this practice having possession of the teachings of the present invention. Accordingly, the present invention should be limited only by the following claims.

I claim:

1. A fluid delivery system for the treatment of subcutaneous hernia sites, comprising:
    (a) a bioabsorbable, polymer fabric mesh layer which is substantially planar in configuration, having an upper side and a lower side;
    (b) a bioabsorbable porous underlay attached to said lower side of said bioabsorbable polymer fabric mesh layer; and,
    (c) a bioabsorbable impermeable bladder having an open portion formed over a portion of said upper side of said fabric mesh layer and attached thereto so that contents of said bladder are in direct contact with said upper side of said fabric mesh at said portion, and in fluid communication with said bioabsorbable porous underlay through capillary pores in said fabric mesh layer.

2. The fluid delivery system of claim 1, wherein said bioabsorbable porous underlay comprises collagen.

3. The fluid delivery system of claim 2, wherein said fabric mesh layer comprises bioabsorbable polymers selected from the group consisting of polylactides, polyglycolides and their copolymers, polyanhydrides, polyorthoesters, polyethylene glycols, and block polymers or copolymers thereof.

4. The fluid delivery system of claim 3, wherein said bladder comprises bioabsorbable polymers selected form the group consisting of polylactides, polyglycolides and their copolymers, polyanhydrides, polyorthoesters, polyethylene glycols, and block polymers or copolymers thereof.

5. The fluid delivery system of claim 4, wherein said bladder contains a fluid with therapeutic medicament.

6. The fluid delivery system of claim 5, wherein said therapeutic medicament is selected from the group consisting of liquid growth factors, antibiotics, anti-inflammatories, analgesics and stem cells.

7. The fluid delivery system of claim 6, further comprising:
    (d) at least one hollow band of bioabsorbable polymer material extending across said bladder and connecting to said polymer fabric mesh layer on either side of said bladder.

8. A method of treating fascia at an incision site, said method comprising the steps of:
    (a) opening skin and subcutaneous fat at said incision site;
    (b) placing the device of claim 1 under said subcutaneous fat; and
    (c) and dispersing liquid from said bladder through said polymer fabric mesh layer to said fascia at said incision site.

9. The method of claim 8, wherein said polymer fabric mesh layer extends beyond said bladder, and further comprises a layer of collagen on a side of said polymer fabric mesh layer opposite said bladder.

10. The method of claim 9, further comprising the step of:
    (d) suturing said polymer fabric mesh layer to said fascia on either side of said bladder.

11. The method of claim 8, wherein said step (a) of opening said skin and said subcutaneous fat includes a sub-step of placing a combined bioabsorbable polymer fabric mesh layer and bioabsorbable bladder beneath an incision in said fascia.

* * * * *